(12) United States Patent
Gambert

(10) Patent No.: US 7,727,368 B2
(45) Date of Patent: Jun. 1, 2010

(54) LEAD FREE GALVANIC OXYGEN SENSOR

(75) Inventor: Rudolf Gambert, Wismar (DE)

(73) Assignee: IT Dr. Gambert GmbH, Wismar (DE)

( * ) Notice: Subject to any disclaimer, the term of this patent is extended or adjusted under 35 U.S.C. 154(b) by 439 days.

(21) Appl. No.: 11/751,232

(22) Filed: May 21, 2007

(65) Prior Publication Data
US 2007/0272553 A1    Nov. 29, 2007

(51) Int. Cl.
*G01N 27/404* (2006.01)
(52) U.S. Cl. .......... 204/415; 204/431; 204/432
(58) Field of Classification Search .......... 204/414, 204/415, 431, 432
See application file for complete search history.

(56) References Cited

U.S. PATENT DOCUMENTS

| 2,638,102 A | | 5/1953 | Goldsmith | |
|---|---|---|---|---|
| 3,429,796 A | * | 2/1969 | Lauer | 204/415 |
| 3,515,658 A | * | 6/1970 | Amdur | 204/415 |
| 3,767,552 A | * | 10/1973 | Lauer | 204/408 |
| 4,483,694 A | | 11/1984 | Takamura et al. | |
| 4,664,119 A | * | 5/1987 | Bessman et al. | 600/359 |
| 4,781,995 A | | 11/1988 | Giner | |
| 4,900,422 A | * | 2/1990 | Bryan et al. | 204/401 |
| 5,855,750 A | * | 1/1999 | Kiesele | 204/415 |
| 2007/0227908 A1 | * | 10/2007 | Barnett | 205/782.5 |

FOREIGN PATENT DOCUMENTS

| DE | 19902509 | * | 11/2000 |
|---|---|---|---|
| GB | 1255353 | * | 12/1971 |
| GB | 1391168 | * | 4/1975 |
| GB | EP0305961 | * | 3/1989 |
| GB | EP0763730 | * | 3/1997 |
| GB | EP1593962 | * | 9/2005 |
| WO | WO93/10444 | | 5/1993 |

* cited by examiner

*Primary Examiner*—Bruce F Bell
(74) *Attorney, Agent, or Firm*—Dinsmore & Shohl LLP

(57) ABSTRACT

A lead free, galvanic sensor. The sensor having a housing, a cathode, an anode, a diffusion barrier, contact wires and an electrolyte, the anode being made of a tin containing alloy. The sensor electrolyte is an aqueous solution of phosphoric acid or an aqueous solution of a cesium salt.

14 Claims, 2 Drawing Sheets

LEAD FREE GALVANIC OXYGEN SENSOR

TECHNICAL FIELD

The invention describes a galvanic oxygen sensor.

BACKGROUND

Galvanic oxygen sensors are widely applied in high volumes in industrial, environmental and medical measurements because of their high reliability, small size, low power consumption and good price performance relation. Starting with their development in the 1950's many instruments to measure oxygen partial pressure were designed, some of them still being used today. In modem instruments like ventilators, emission monitoring devices and automotive emission testers such sensors are still preferred for oxygen measurements.

Typically, the sensors comprise a housing, a cathode, an anode having a bigger surface than the cathode, a diffusion barrier, an electrolyte and contact wires to connect the cathode and the anode electrically. The anode generates the required electrochemical potential for the reduction of oxygen at the cathode. Such galvanic sensors are described in U.S. Pat. No. 3,767,552 and U.S. Pat. No. 3,429,796.

GB 1255353 describes a galvanic oxygen sensor with an anode material being made of lead, tin, cooper and their alloys. The electrolyte of this sensor contains sulfides. This design leads to very stable sensor signals that can be amplified electronically very well. On the other hand it is a considerable drawback of this design that the sensor can not be used in acid gas atmospheres containing e.g. carbon dioxide. In this case poisonous sulfur dioxide is can be released. Therefore the sensor can not be used for medical applications.

GB 1391168 describes a device for the measurement of oxygen. This device has two oxygen permeable membranes, one of them being porous, a silver cathode, and a tubular tin anode. This configuration allows the device to measure in condensing media or atmospheres that contain water droplets like in humidifiers for breath. The porous membrane prevents, due to its hydrophobic properties, the formation of a closed water film on the surface which could cause a signal reduction. The composition of the electrolyte is not described in the application. The principle to use a combination of two membranes, one of them being porous and thus preventing water condensation is state of the art for oxygen sensors today.

EP 1 593 962 describes a lead free galvanic oxygen sensor with an anode being made of zinc or aluminum. The inventors of this '962 patent document admit that these materials corrode and thus are only stable within a narrow pH-range of the electrolyte. Such sensors have a very limited lifetime when they are used at elevated temperatures because the corrosion is very temperature dependent. Additionally, the corrosion process generates water that has to be removed from the sensor. This can lead to a complex design of the sensor housing.

For a galvanic oxygen sensor with electrolyte and anode, the equations for the electro-chemical reactions are as follows.

Equation for the electrochemical process at the cathode with an alkaline electrolyte:

$$O_2 + 2H_2O + 4e^- \rightarrow 4OH^-$$ (Eq. 1a)

In an acid electrolyte the reduction of oxygen consumes protons:

$$O_2 + 4H^+ + 4e^- \rightarrow 2H_2O$$ (Eq. 1b)

Equations for possible electrochemical processes at the anode depending on the actual pH at the anode surface:

$$Me + 4OH^- \rightarrow MeO_2 + 4e^- + 2H_2O$$ (Eq. 2a)

$$2Me \rightarrow 2Me^{2+} + 4e^-$$ (Eq. 2b)

Me stands for any metal that may exist at bivalent or tetravalent oxidation stage after the oxidation. According to equation 2a, the oxidation of the anode material leads to an oxide. According to equation 2b, the oxidation of the anode material leads to a soluble salt.

In EP 0305961, buffered weak acid electrolytes are described that consist of organic acids and their salts leading to oxygen sensors with increased lifetime.

The diffusion membrane in a sensor is a barrier for the gas so that a diffusion limiting current is generated at the cathode that can be measured. The diffusion limited current is proportional to the gas partial pressure at the diffusion barrier by the first approximation.

Instead of a membrane, a metal or plastic disc with a very small central hole can also be used. Given the appropriate dimension of the hole, the diffusion of the oxygen happens according to the Knudsen principle. This also leads to a diffusion limited current as long as all oxygen molecules reaching the cathode are being reduced. In this case, the sensor signal is proportional to the oxygen concentration at the sensor head. A device based on this principle is described in EP 0763730.

The electrical current flowing through the galvanic cell depends linearly on the oxygen partial pressure or the oxygen concentration. The electrochemically active surface of the anode should be bigger than the surface of the cathode to ensure an adequate motive force for the reaction and to avoid a concentration polarization at the surface of the anode.

In practice, lead is the state of the art anode material. It has a high hydrogen overvoltage and is thus corrosion resistant in alkaline and weak acid electrolytes over a wide temperature range. The relative high density of the lead permits small designs of the anode. In addition, it can be shaped easily due to its softness and is available in high purity at a relatively low price.

However, for some years lead has been disliked as a construction material. It is known that relatively low chronic doses are harmful to the human nervous system, the hematopoietic system and the kidneys. Thus, the limits for lead and lead containing substances in the environment have been repeatedly lowered in the past years. New legislation in various countries and states prohibits the use of lead in solders and electronic components. Also other heavy metals like cadmium and mercury are banned by the European Union's RoHS (Restriction of Hazardous Substances), and as such they are not viable alternatives to be used in electrochemical oxygen sensors.

As such, there is an need for a lead free, galvanic oxygen sensor.

SUMMARY

The present invention relates to a new and improved oxygen sensor.

One aspect of the present invention is a galvanic oxygen sensor with a lead free anode which is electronically and mechanically compatible with existing lead containing sensors. By this way, existing instruments can further rely on the advantages of this technology as well as new instruments can be fitted to it.

One exemplary embodiment of the present invention is a galvanic oxygen sensor comprising: a housing, a cathode, an anode, a diffusion barrier, contact wires and an electrolyte, wherein said anode is made from a tin containing alloy and wherein the anode is substantially free of lead. The galvanic oxygen sensor of the present invention is advantageous for providing an effective oxygen gas sensor without utilizing a lead containing anode. These and additional advantages will be apparent in view of the detailed description.

BRIEF DESCRIPTION OF THE DRAWINGS

While the specification concludes with claims particularly pointing and distinctly claiming the present invention, it is believed that the same will be better understood from the following description taken in conjunction with the accompanying drawings in which:

Figure 1:
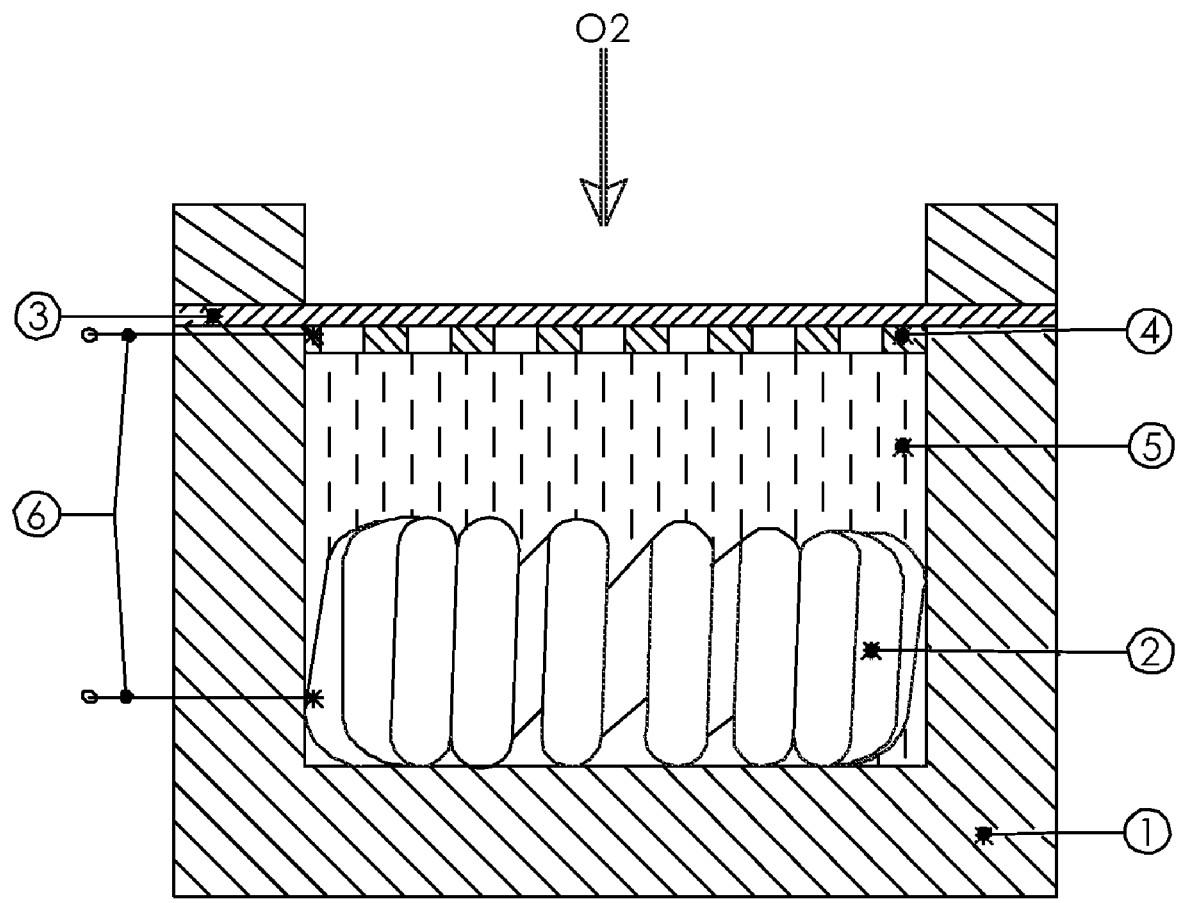
FIG. 1 is a schematic illustration of an exemplary sensor according to a first embodiment of the present invention.

The embodiments set forth in the drawings are illustrative in nature and not intended to be limiting of the invention defined by the claims. Moreover, individual features of the drawings and the invention will be more fully apparent and understood in view of the detailed description.

DETAILED DESCRIPTION

Reference will now be made in detail to various embodiments of the invention, examples of which are illustrated in the accompanying drawings.

All percentages, ratios and proportions herein are on a weight basis unless otherwise indicated. Except as otherwise noted, all amounts including quantities, percentages, portions, and proportions, are understood to be modified by the word "about", and amounts are not intended to indicate significant digits. Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The apparatuses of the present invention can comprise, consist of, and consist essentially of the essential elements and limitations of the invention described herein, as well as any of the additional or optional components or limitations described herein.

A pre-condition for the functioning of an electrochemical sensor is that all oxygen molecules diffusing to the cathode are reduced electrochemically. This can only be achieved when the anode is electro positive enough, thus enough electrons for the oxygen reduction are available. On the other hand the anode material shall not be too electro positive, because this would lead to hydrogen generation at the cathode. In this case, the sensor could consume itself quickly. In addition there could be a base current interfering with the sensor signal. The generation of hydrogen can be influenced by the composition of the electrolyte and the composition or coating of the cathode, but only to a minor extent.

The temperature dependency of the electrochemical potentials can make the conditions even more complex. Typically, the working range or allowed range for the sensors is between −20° C. and 60° C., meaning a range of 80 Kelvin, in which the working point of the anode must be stable. Otherwise, hydrogen could be generated or the oxygen could be reduced at the cathode only partially leading to a non linear sensor signal.

Another risk is the corrosion resistivity of the anode material within the specified operating temperature range. The typical lifetime of conventional sensors is between 2 to 3 years and the new sensors have to last at least as equally long. Such a lifetime can only be achieved when the metal is either protected by an oxide layer or the generation of a salt with low solubility on its surface. It is important that this layer stays conductive throughout the whole lifetime of the sensor otherwise, the electrochemical reaction would be limited or even stopped.

The idea of an adjustable electrochemical potential by the composition of the alloy involves some risks as alloys tend to form inter metallic phases and eutectic. These have often different properties compared to the homogeneous mixed phases. Unfortunately, such information is typically not available in the literature. Thus electrochemical properties can typically only be calculated by approximation and thus must be determined experimentally.

Surprisingly binary alloys made of tin and silver or copper and especially tertiary alloys made of tin, silver and copper have excellent properties in phosphoric acid electrolytes. Tin as pure metal leads to hydrogen generation at the cathode in acid electrolytes and thus can not be used for this purpose. Already small percentages of silver or copper in the tin alloy reduces the electro positive properties of the tin. It has been shown that even an amount of 0.1 to 3% of silver and/or copper are sufficient to cut down the hydrogen formation over the whole operating temperature range to an acceptable extent. Also higher amounts of silver or copper in the alloy are possible but with regard to the yield of the material and in view of the manufacturing cost, they are less attractive.

The alloys are largely corrosion resistant over the relevant temperature range and generate a sufficient electrochemical potential to reduce the oxygen at the cathode. This works especially well when silver or gold plated etched parts are used as cathode material, their basic material being a copper alloy with a part of iron or phosphor. These are characterized by good mechanical properties, good electrical conductivity and can be coated galvanic with gold or silver layers that are dense and adhere very well.

In case low sensor currents are desirable, a fine wire or a small band made of silver, gold or silver plated copper are adequate cathodes. It should be placed directly behind the diffusion membrane, in contact with the electrolyte and have a contact wire that is threaded through the housing to the outside. The contact wire can be glued to the housing, welded ultrasonic or thermal with the plastic to avoid any leaking of the electrolyte from the housing. The passageway of the contact wire should be configured such that a minimum amount of its surface is in contact with the electrolyte. As small amounts of oxygen are solved in the electrolyte, this area would contribute to the base current of the sensor and impair the sensor behavior in atmospheres with low oxygen content.

The composition of the electrolyte influences the function of the sensor as well. In combination with the described anode materials, the best results can be obtained with strong phosphoric acid solutions. These solutions have weak hygroscopic properties beside their good electrochemical properties. The hygroscopic properties counteract a drying out of the electrolyte when the sensor is exposed to dry working conditions, thus contributing to a long lifetime of the sensor even at tough ambient conditions.

Solutions with higher pH can be used as well in case a long sensor lifetime is of less importance. In this case, phosphoric acid solutions buffered with their salts can be used as electrolyte. It has been shown that solutions with a pH up to 7 gave good results.

With a pH above 7, pure tin can be used as an anode material, but then the hydrogen formation starts at lower temperatures than with doped tin. Very good results can be obtained with aqueous solutions of cesium salts, especially with cesium hydroxide, cesium carbonate, cesium hydrogen carbonate and cesium acetate, or a mixture of them. These salts have very good solubility in water, are partially hygroscopic and contribute to a long lifetime of the sensor. At higher concentrations, the amount of oxygen dissolved in the electrolyte can be reduced due to the good solubility of the cesium salts. This leads to short response times and a low base current of the sensor.

It has been found that the addition of anionic or cationic tensides to the electrolyte is beneficial. These secure good wetting of all surfaces in the sensor and thus leads to a very repeatable sensor behavior. Amongst others, Triton X-100 and QS-44 can be used as tensides.

Sensors manufactured in this way show a stable and linear signal to the partial pressure of oxygen over a wide temperature range. The sensor current can be controlled by the configuration of the cathode surface in such a way that it is compatible to the sensors with lead anodes that exist on the market today. This guarantees the backwards compatibility that is required for instruments which are already on the market.

The design geometry of the anode can be as described in DE 199 02 509. This ensures a steady consumption of the anode.

On exemplary embodiment of the present invention is a galvanic, electrochemical sensor, illustrated in FIG. 1, comprising of a housing (1), an anode (2) being made of an alloy of tin with a silver content of 2% and a copper content of 1%. The anode has a weight of 2 grams. Further the sensor has a diffusion membrane of polytetrafluoroethylene (3) a cathode (4) of a silver plated galvanic part, being made of an alloy of copper with a content of 2.25% iron and 0.002% phosphor (manufacturer Wieland GmbH, type K65). The electrolyte (5) consists of phosphoric acid (85%) with a water content of 15%. In addition there are contact wires (6) for the electrodes that are threaded through the housing to the outside. Thus an electrical current is generated that represents the measurement signal. The electrical current flowing through a resistor is proportional to the oxygen partial pressure at the diffusion membrane. The cathode has a surface of about 7.5 mm$^2$. The diffusion membrane has a thickness of about 20 μm and generates a sensor signal of about 8 μA in air. When nitrogen is fed to the sensor the signal goes down to about 30 nA. When oxygen is fed to the sensor nearly the theoretical value of about 38 μA is reached.

The oxygen that diffuses through the membrane (3) reaches the cathode where it is reduced. At the anode (2), metal ions get dissolved according to Faradays law or the metal is turned into its metal phosphate.

Figure 2:
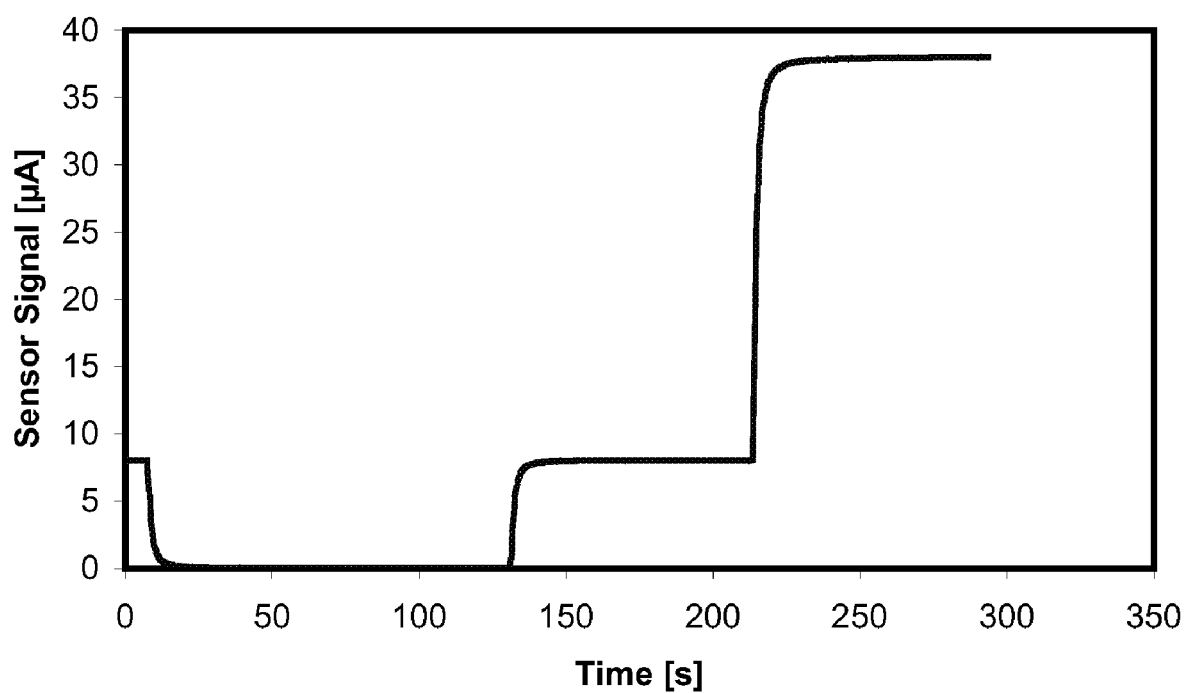
FIG. 2 is a exemplary sensor signal at different partial pressures of oxygen according to one embodiment of the present invention.

As can be seen from FIG. 2 such a sensor has an excellent linearity for the oxygen partial pressure. The plot shows the sensor current at air, at nitrogen and air with nitrogen. The signal at oxygen is 4.8 fold higher than the signal at air and complies with the theoretical value. The lifetime of the sensor can be calculated by approximation. Assuming a mean sensor current of 20 μA, 2 g anode material as tin with a content of 3% for the alloy, an efficiency of 80%, a molecular weight for tin of 116.7 g/mol and an oxidation of the tin to $Sn^{2+}$, then a charge of 2500 As or a nominal lifetime of $1.3 \times 10^8$ s or 4 years can be calculated according to Faradays law. Long term tests with increased oxygen partial pressure have shown that these values can be reached in practice.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What claimed is:

1. A galvanic oxygen sensor comprising: a housing, a cathode, an anode, a diffusion barrier, contact wires and an electrolyte, said anode being made from a tin containing alloy and wherein said anode is substantially free of lead.

2. The galvanic oxygen sensor according to claim 1, wherein the electrolyte is an aqueous solution of phosphoric acid with a concentration between 65% and 95%.

3. The galvanic oxygen sensor according to claim 1, wherein the anode material is an alloy from tin with silver and/or copper, the amount of silver and copper being at least 0.1% and at maximum 25% of the overall mass.

4. The galvanic oxygen sensor according to claim 2, wherein the anode material is an alloy from tin with silver and/or copper, the amount of silver and copper being at least 0.1% and at maximum 25% of the overall mass.

5. The galvanic oxygen sensor according to claim 1, wherein the electrolyte comprises an aqueous solution of cesium salts.

6. The galvanic oxygen sensor according to claim 5, wherein the cesium salts comprise cesium hydroxide, cesium carbonate, cesium hydrogen carbonate, cesium acetate or a combination thereof.

7. The galvanic oxygen sensor according to claim 1 wherein the electrolyte contains anionic or cationic tensides.

8. The galvanic oxygen sensor according to claim 2, wherein the electrolyte contains anionic or cationic tensides.

9. The galvanic oxygen sensor according to claim 3, wherein the electrolyte contains anionic or cationic tensides.

10. The galvanic oxygen sensor according to claim 4, wherein the electrolyte contains anionic or cationic tensides.

11. The galvanic oxygen sensor according to claim 5, wherein the electrolyte contains anionic or cationic tensides.

12. The galvanic oxygen sensor according to claim 1, wherein the cathode comprises a silver or gold coated copper alloy.

13. The galvanic oxygen sensor according to claim 12, wherein the cathode is an etched part.

14. The galvanic oxygen sensor according to claim 1, wherein the electrolyte has a pH of less than 7.

* * * * *